United States Patent [19]

Couchman

[11] 4,294,122
[45] Oct. 13, 1981

[54] FASTENER INCORPORATING ULTRASONIC TRANSDUCER

[75] Inventor: James C. Couchman, Fort Worth, Tex.

[73] Assignee: General Dynamics Corporation, Fort Worth, Tex.

[21] Appl. No.: 57,059

[22] Filed: Jul. 12, 1979

[51] Int. Cl.³ .................. F16B 31/02; G01N 24/00
[52] U.S. Cl. .................................................. 73/761
[58] Field of Search .................. 73/761, 629, 597; 116/DIG. 34; 310/336

[56] References Cited

U.S. PATENT DOCUMENTS

| Re. 30,183 | 1/1980 | Popenoe | 73/761 |
| 3,201,977 | 8/1965 | Kutsay | 73/761 |
| 3,759,090 | 9/1973 | McFaul et al. | 73/761 |
| 4,014,208 | 3/1977 | Moore et al. | 73/761 |
| 4,127,788 | 11/1978 | Daugherty | 73/761 |

Primary Examiner—Anthony V. Ciarlante
Attorney, Agent, or Firm—Arthur F. Zobal

[57] ABSTRACT

A threaded bolt having an opening in either its head or its opposite end with an ultrasonic transducer fixedly secured therein for use in obtaining preload measurements as well as other measurements for quality control inspection or for monitoring purposes.

29 Claims, 10 Drawing Figures

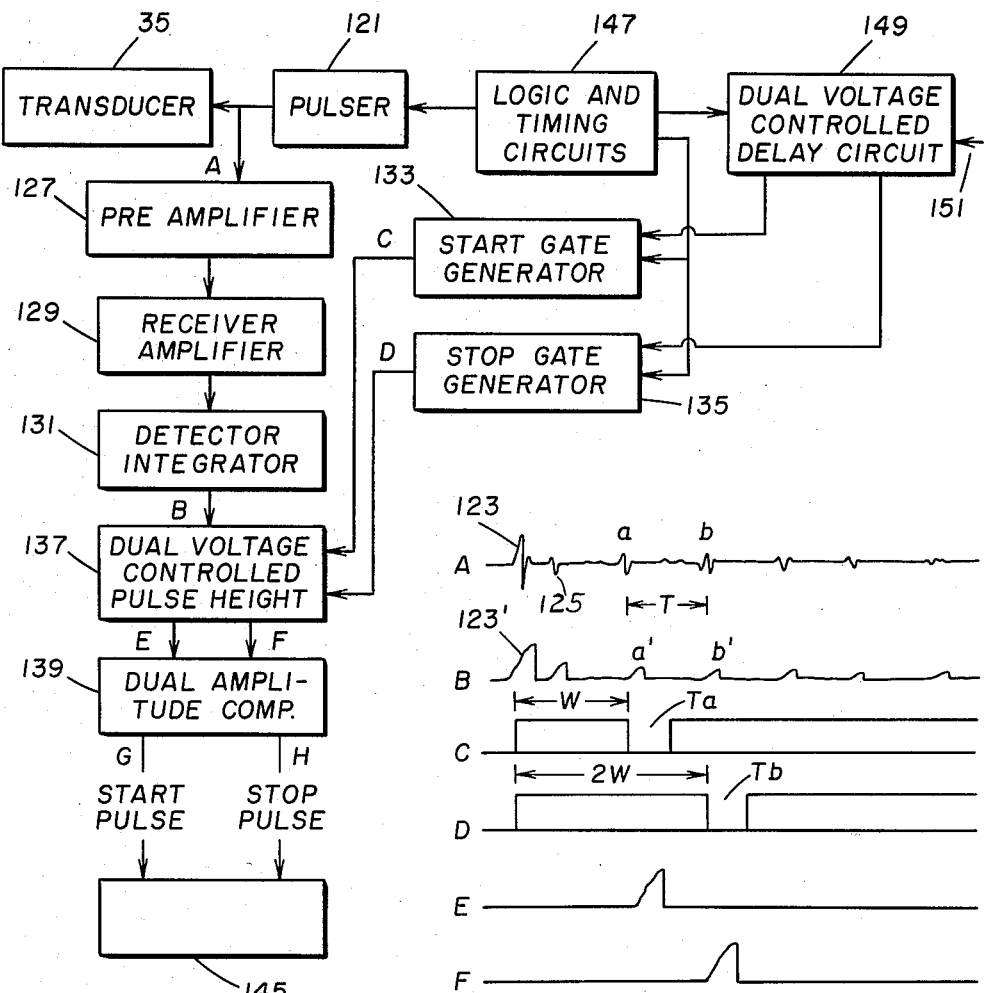

FASTENER INCORPORATING ULTRASONIC TRANSDUCER

The Government has rights in this invention pursuant to Contract No. F33615-76-C-5251 awarded by the Department of the Air Force.

FIELD OF THE INVENTION

The present invention relates to the measurement of preload on a threaded fastener and more particularly to a threaded fastener incorporating an ultrasonic transducer for allowing accurate measurements of preload to be obtained as well as other measurements for quality control inspection or for monitoring purposes.

DESCRIPTION OF THE PRIOR ART

In aircraft, space vehicles, and other types of vehicles, it is important that bolt fasteners be properly preloaded (tightened) to prevent structural failure. This is particularly true with respect to fasteners employed in critical load bearing structures. It has been found that the conventional hand operated torque wrench may result in errors of 30% or higher in pretensioning a bolt to the desired preload. Thus means is desired that will accurately measure the true preload on a bolt.

Pulse-echo and resonant frequency techniques have been developed to obtain more accurate measurements of the preload obtained on a bolt when torqued. Pulse-echo techniques are disclosed in U.S. Pat. Nos. 3,759,090 and 3,969,810 and a resonant frequency technique is discussed by Heyman, J. S., "Ultrasonic Bolt Stress Monitor" Industrial Research, Oct. 1976; Lutz-Nagey, R. C., "Torque Verification from Eyeball to Accuracy", Automation, October 1976; and Langley Research Center, "ROUS Bolt Tensioning Monitor," NASA Tech Briefs, Summer 1976. The pulse-echo technique is preferred over the resonant frequency technique since it is more accurate and allows measurements to be otained faster.

In the prior pulse-echo and resonant frequency techniques, an ultrasonic transducer is clamped to the head of the bolt with an acoustic coupling oil or medium located between the transducer and the bolt. U.S. Pat. No. 3,759,090 disclosed a manual clamping technique while U.S. Pat. No. 3,969,810 discloses an automatic torque wrench which carries the transducer in the wrench head and allows measurements to be obtained while torquing.

Manually clamping the transducer in place for each test has disadvantages since it is time consuming and difficult to properly position the transducer with respect to the bolt head to obtain optimum signals. An automatic torque wrench which carries the transducer in the wrench head has the same problems in positioning the transducer with respect to the bolt head to obtain optimum signals and also results in slippage between the transducer and the bolt head during torquing. In the pulse-echo technique, this slippage introduces a time error which even though only a few nanoseconds, is enough to prevent accurate time measurements.

SUMMARY OF THE INVENTION

It is an object of the present invention to provide a fastener incorporating an acoustic transducer as by being built into its head or threaded end to obtain more accurate preloading measurements and also to provide for improved quality control inspection of the fastener and to allow acoustic monitoring of critical fasteners.

It is a further object of the present invention to provide a method of employing a fastener having an acoustic transducer permanently attached to its head or threaded end for obtaining accurate measurements of preload as well as other measurements for quality control inspection or for monitoring purposes.

In the embodiment disclosed, the fastener has an opening formed in its head or threaded end with the transducer located and secured therein.

BRIEF DESCRIPTION OF DRAWINGS

FIG. 8 is an electrical block diagram of a system for obtaining preload or other measurements.

FIG. 9 are timing diagrams useful in understanding the system of FIG. 8, and

DESCRIPTION OF THE PREFERRED EMBODIMENTS

Figure 1:
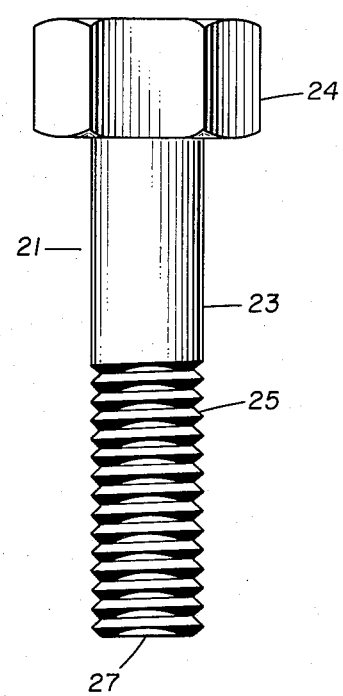
FIG. 1 illustrates a coventional threaded fastener.

Referring now to FIG. 1 of the drawings, reference numeral 21 identifies a conventional metallic fastener or bolt used in aircraft, space vehicles, and in other types of vehicles for securing structural members together. It may be formed of steel, titanium, aluminum, or other metals or alloys. The fastener comprises a shank 23 having a head 24 formed at one end and threads 25 formed at the other end 27 to which a nut may be threaded.

Figure 2:
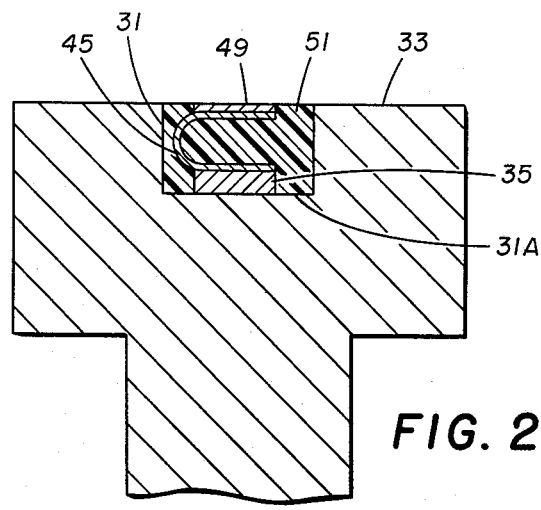
FIG. 2 is an enlarged cross section of the head of the fastener of FIG. 1 illustrating a transducer secured in the head.
Figure 3:
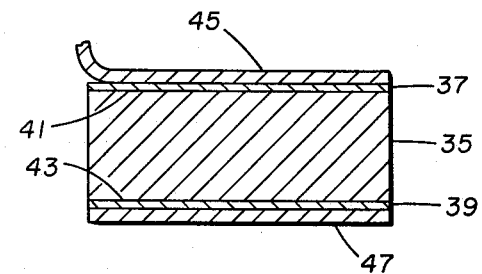
FIG. 3 is an enlarged cross sectional view of the transducer of FIG. 2.

Referring to FIGS. 2 and 3, a cyclindrical opening 31 is formed in the head from its flat surface 33 inward toward the shank. Located and secured in the opening is an ultrasonic transducer 35 formed of a piezoelectric material such as Pb Zr Ti. The transducer is disc shaped and as shown also in FIG. 3 has thin layers of electrically conducting metal 37 and 39 secured to opposite ends or surfaces 41 and 43 respectively. Layers 37 and 39 may be secured to ends 41 and 43 by conventional techniques. Secured to the layers 37 and 39 are electrodes 45 and 47 respectively which may be tin strips secured in a conventional manner. Layers 37 and 39 and electrode 47 are not shown in FIG. 2 for purpose of clarity. The transducer 35 is located and secured in the opening 31 such that the electrode 47 is in electrical contact with the flat lower surface 31A of the opening 31 and hence it is in electrical contact with the fastener 21. The transducer 35 may be secured in place with an adhesive or epoxy. The upper electrode 45 extends upward to an upper metal plate 49 which has its upper surface flush with the upper surface 33 of the bolt head 24. The remainder of the space in the openings 31 is filled with a suitable potting material 51 which is of the type that will damp out ultra sound vibrations traveling toward the plate 49. After the transducer 35 is located and secured in place in the opening 31, the potting material may be poured in the opening in a fluid state after which it is allowed to cure. After curing, it will contribute to holding the transducer in place in the opening 31.

For use for obtaining pulse-echo time measurements, a pulsing and receiving circuit will be electrically coupled to the plate 49 and its ground lead will be electrically coupled to the bolt 21 whereby the bolt itself will act as a ground return.

With the transducer secured to the bolt head as described in connection with FIGS. 2 and 3, the slippage problem is eliminated thereby allowing accurate measurements to be obtained while torquing with an automatic torque wrench of the type disclosed in U.S. Pat. No. 3,969,810. Since the transducer is built into the fastener, a thinner transducer may be employed which produces a higher frequency and results in more accuracy. Moreover, a permanent record may be obtained of each preload.

Figure 4:
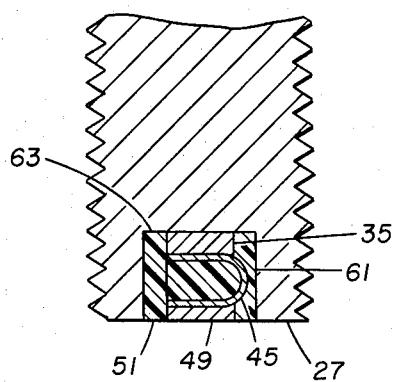
FIG. 4 is an enlarged cross section of the threaded end of the fastener of FIG. 1 illustrating a transducer secured in the threaded end.

Referring to the embodiment of FIG. 4, the transducer 35 is shown secured in a cyclindrical opening 61 formed in the end 27 of the fastener 21 opposite the head 24. The transducer 35 is the same as that shown and described in connection with FIGS. 2 and 3. Layers 37 and 39 and electrode 47 are not shown in FIG. 4 for puspose of clarity. The transducer will be attached in the opening 61 such that its electrode 47 is in electrical contact with the flat surface 63 of the opening 61 and is embedded in the opening 61 with a potting material 51. It may be used in the same manner as when attached in the head 24 except that when used to obtain preload measurements during torquing, a separate tool will be employed to obtain electrical connection between the pulse-echo circuit and the plate 49. The embodiment of FIG. 4 will not be employed when the fastener is torqued into a threaded opening formed in a structural member.

Figures 5, 6:
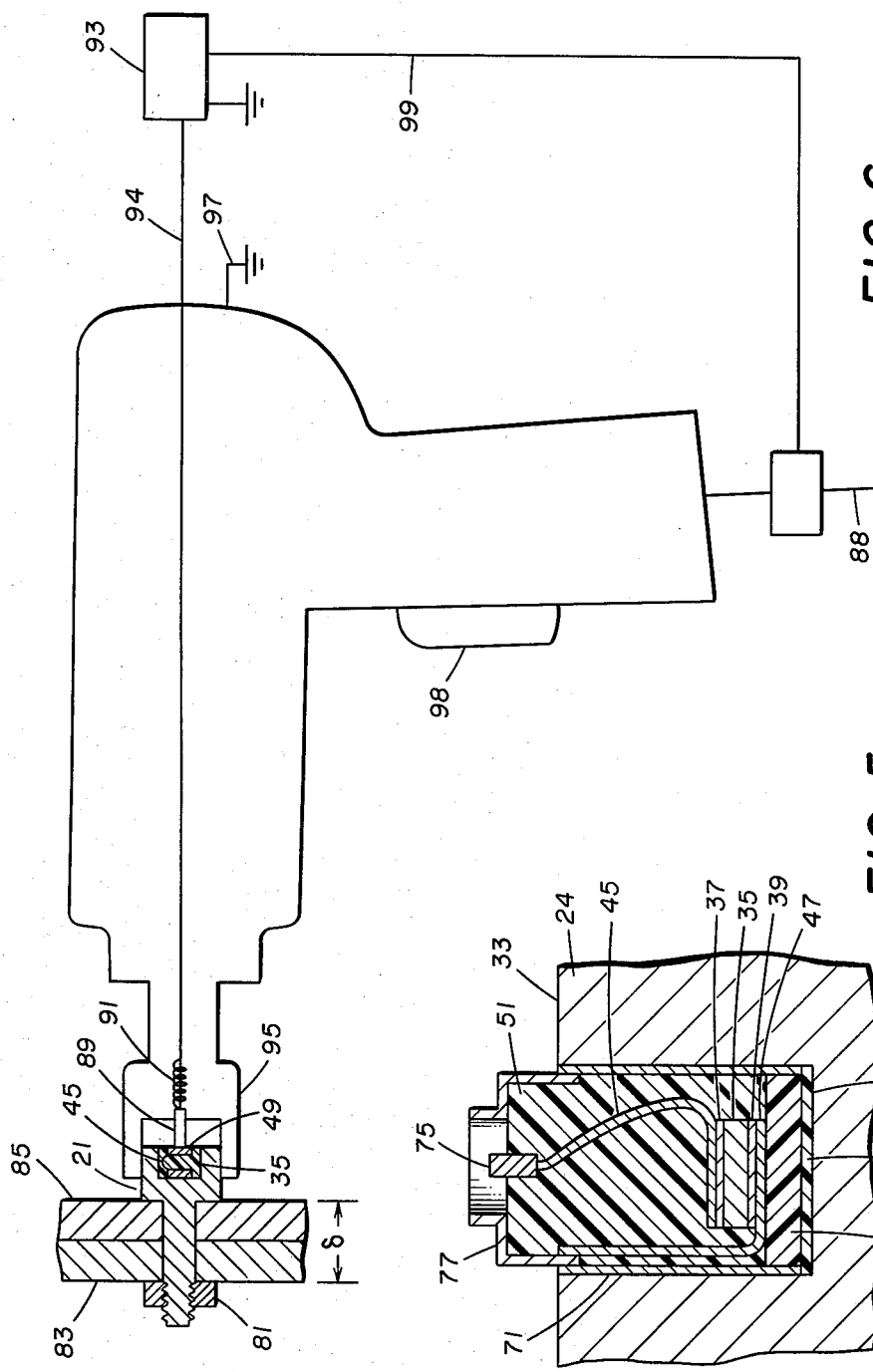
FIG. 5 illustrates another embodiment of the present invention with the transducer built into the head or threaded end of the fastener in a different manner.
FIG. 6 illustrates an automatic torque wrench torquing one embodiment of the fastener of the present invention in place while preload measurements are obtained.

In the embodiment of FIG. 5, neither of the electrodes of the transducer 35 are in direct contact with the bolt 21. The transducer 35 is mounted in a cyclindrical member 71 which may be formed of metal or plastic. Secured within the lower ends of member 71 is a layer of material 73 (which may be a suitable plastic) having good acoustic coupling properties. The transducer 35 is located such that its electrode 47 rests against layer 73 and is embedded in the member 71 by the potting material 51 which has good acoustic damping properties. Electrode 45 is in electrical contact with a metallic pin terminal 75 held in place by the potting material 51. Electrode 47 extends upward and is electrically connected to a metallic cyclindrical terminal 77 which in turn is secured to member 71. Member 71 is secured in the opening 31 of the bolt head with a suitable glue or epoxy. A layer of oil or grease 79 is located between layer 73 and the lower surface 31A of opening 31 for purposes of acoustic coupling. In using the embodiment of FIG. 5 for preload measurements, a pulsing and receiving circuit will be electrically coupled to terminal 75 and terminal 77 will act as a return terminal. It is to be understood that member 71 with its transducer 35 may be secured in the opening 61 of the threaded end 27 of the bolt 21 instead of in opening 31 of the bolt head.

Pulse-echo time measurements for preload may be made with the embodiments of FIGS. 2–5 whether the fastener is torqued with an automatic wrench or with a manual wrench. In FIGS. 6, the bolt 21 and a nut 81 are employed to fasten together two plates 83 and 85. The bolt 21 employs the embodiment of FIGS. 2 and 3. A power driven wrench 87 is shown in outline form for torquing the fastener and the nut 81 together. The means for holding the nut 81 is not shown. The wrench 87 may be pneumatically driven or electrically driven. Reference numeral 88 identifies pneumatic or electrical lines for applying power to the wrench. A terminal 89 is biased against plate 49 by a spring 91 and is electrically connected to a pulse-echo measuring system 93 by lead 94. The socket 95 of the wrench 87 is in electrical contact with the head 24 of the bolt and the wrench 87 is grounded at 97. When good pulse-echo signals are being detected within the desired time window or windows, a light will turn on signaling to the operator to actuate the trigger 98 to apply power to the wrench to tighten the bolt. When the desired preload or stress is achieved, the system 93 issues a command by way of line 99 to cut off power to the wrench. It too much stress is measured, the system 93 will issue a command to the wrench (by means not shown) to back off until the desired stress is achieved.

When the fastener has been tightened to the desired preload, the socket 95 of the wrench 87 is removed and the transducer 35 left in place in the fastener. It may be used at a later time to recheck preload or to detect for flaws or cracks or to monitor for acoustic emissions resulting from structural failure.

Figure 7:
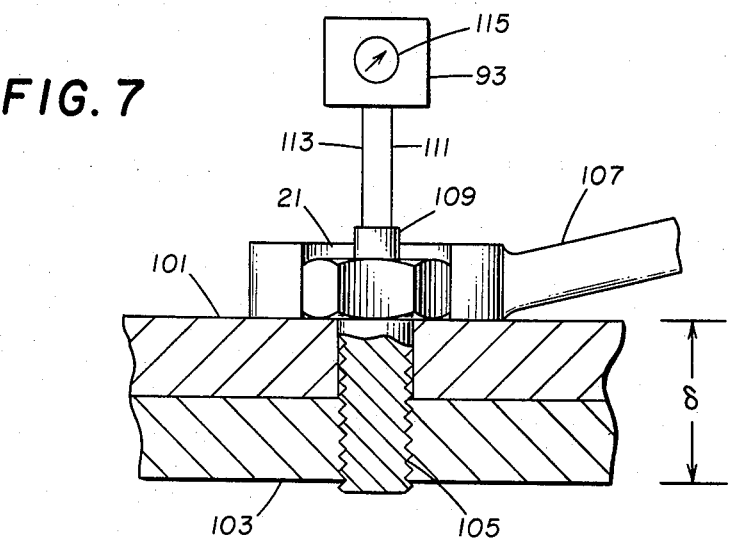
FIG. 7 illustrates a hand wrench torquing another embodiment of the fastener of the present invention in place while preload measurements are obtained.

In FIG. 7, the bolt 21 is employed to fasten together plates 101 and 103, the latter of which has threads 105 formed within its aperture. The bolt 21 employs the embodiment of FIG. 5. A manual wrench 107 is shown for torquing bolt 21 into threads 105 for fastening together plates 101 and 103. An electrical socket 109 is fitted to terminals 77 and 75 for connecting these terminals repsectively to leads 111 and 113 which extend to the pulse-echo measuring system 93. A meter 115 is employed to measure torque by the pulse-echo technique while the bolt 21 is being torqued by wrench 107. When the desired preload is achieved, the wrench 107 is removed and the transducer 35 is left in place in the bolt. It may also be used at a later time to recheck preload or to detect for flaws or cracks in the bolt or to monitor for acoustic emissions resulting from structural failure.

Referring now to FIGS. 8 and 9, there will be described a preferred pulse-echo technique for measuring preload stress. For these measurements, the transducer will have a frequency of from 0.5 MHZ to 200 MHZ. A pulser 121 is employed for pulsing the transducer at a repetition rate of 100–2000 pulses per second. Each time the transducer is pulsed, an acoustics signal will travel to the end of the bolt and back a number of times until the signal is attentuated or damped out. Preferably the first and second back echos (signals reflected from the other end of the fastener) are measured and the time difference between the signals is determined. In FIG. 9A, 123 represents an acoustic pulse generated by the transducer 35 when it is pulsed. The first back echo is identified at a and the second back echo is identified at b. Signal 125 is an echo signal due to reflections from interfaces between coupling layers if such layers are employed. For example, in FIG. 5 such a signal will be produced from interfaces between layers 73, 79, and 31A. The signals to the right of signal b are third, fourth, and fifth back echo signals. The times of the first and second back echo signals a and b are measured and the differences obtained to subtract out the travel times in any acoustic medium employed. The time difference is indicated to be equal to T. The time T is measured prior to preload to obtain $T_O$ and during torquing to obtain $T_t$. The difference between $T_t$ and $T_O$ is found to obtain $\Delta T$ as follows.

$$\Delta T = T_t - T_O \tag{1}$$

It can be shown that stress S on the bolt is equal to $$S = \frac{M}{\delta + \alpha D} \Delta T \tag{2}$$

wherein: M is a material constant, $\delta$ is the grip length (See FIGS. 6 and 7), D is the diameter of the shank of the fastener, and $\alpha$ is an empirically determined parameter which corrects for stress distribution in fasteners. This has been experimentally determined for typical high strenght steel fasteners to be about 0.6.

In obtaining measurements of the first and second back echo signals a and b, two electronic time windows are set following the pulse 123 where signals a and b are expected to occur. The position of these windows depend upon the length of the fastener and the velocity of sound in the material of the fastener. Thus, knowing the properties of the material of the fastener, its length and diameter, and the grip length, one can measure $\Delta T$ to measure stress to obtain an accurate measure of bolt preload.

Referring again to FIGS. 8 and 9, the output of transducer at A is shown in FIG. 9A. This output is applied to a pre-amplifier 127, a receiver amplifier 129, and a detector integrator 131 whose output is shown in FIG. 9B. Detector integrator 131 is a full wave rectifier and integrator. Start and stop gate generators 133 and 135 produce gating singals at times $T_a$ and $T_b$ when the first and second back echo signals are expected respectively. Their outputs are shown in FIGS. 9C and 9D respectively. Dual voltage controlled pulse height circuit 137 converts the first and second back echo signals passed to it at times $T_a$ and $T_b$ to the same heights to correct for attentuation in the fastener. The output of circuit 137 at E and F are shown in FIGS. 9E and 9F respectively. These output signals are applied to dual amplitude comparitor circuit 139 where they are converted to square wave signals shown at 141 and 143 in FIGS. 9G and 9H respectively. These signals then are applied to a time interval counter 145 which counts the time between the leading edges of square wave signals 141 and 143 to obtain t. The leading edge of square wave length 141 turns on the counter and the leading edge of square wave signal 143 turns it off. As stated above, $T_O$ is measured prior to preload and $T_t$ is measured during torquing to obtain $\Delta T$ and hence stress. Circuitry will be provided for averaging $\Delta T$ over a plurality of cycles and for automatically solving for equation 2.

In the system of FIG. 8, pulser 121 is a free-running pulser which produces a pulse at a repetition rate of 100–2000 pulses per second. The logic in timing circuits 147 senses each pulse and sends a signal to start the two gate generators 133 and 135 during each cycle. It also sends a signal to the dual voltage controlled delay circuit 149 which starts two timers. The timers may be charging capacitors, one of which charges at a rate twice as fast as the other. A voltage representative of the two way travel time between the transducer and the other end of the fastener is applied to circuit 149 at 151 and compared with the voltages of the timers. When the voltages of the timers reach the level of the input voltage at 151, the timers are cut off and their associated gate generators are caused to generate the gating signals $T_a$ and $T_b$.

In order to detect for flaws or cracks in the fastener, one merely needs to look at the output of the detector integrator 131 on a oscilloscope or readout. The absence of one or both of the signals a' and b' or changes in their heights indicates possible flaws in the fastener. The appearance of another signal between 123' and a' indicates that the fastener has a crack in it.

Figure 10:
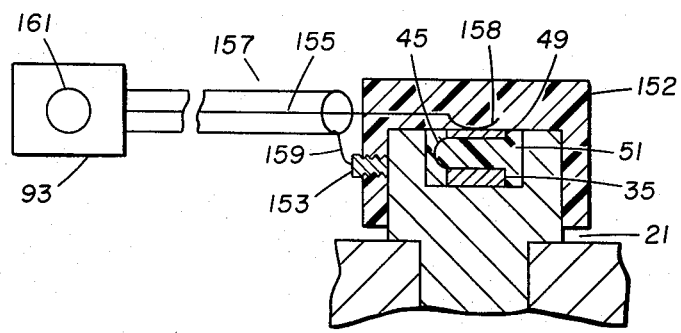
FIG. 10 illustrates a system for monitoring one embodiment of the fastener.

One may use the embodiments of FIGS. 2–5 to look for acoustic emissions while the craft is in flight and which may result from bolt or adjacent structural failure. In this embodiment, the pulser 121 will not be employed. The output of the transducer will be coupled to circuits 127, 129, and 131 and the output of circuit 131 will be monitored. FIG. 10 illustrates one way in which acoustic emissions, which may occur while in flight due to bolt or adjacent structural failure, may be monitored. The embodiment of FIGS. 2 and 3 is shown in this figure. Layers 37 and 39 and electrode 47 are not shown for purposes of clarity. A plastic cap 152 is attached over the bolt head 24 of a critical fastener 1. Attachment is by way of a metal set screw 153. Lead 155 of coaxial cable 157 is coupled to the plate 49 by way of contact 158 and the outer shield of the cable 157 is attached to set screw 153 by way of lead 159. The cable is coupled to system 93 having a readout 161 for monitoring for acoustic emissions from the bolt or from the adjacent craft structure.

The system of FIG. 10 also may be used to allow one to monitor for cracks or flaws in critical fasteners periodically or continuously while in flight. In this embodiment, the pulser 121 will be employed and the output of the detector integrator 131 will be monitored as described previously.

Since the transducer is built into the fastener in the embodiments of FIGS. 2–5, improved quality control can also be obtained. In this respect, the fastener can be tested prior to use to determine if good echo signals are received or if other noise signals appear as described above. If flaws or cracks exist, the fastener may be discarded.

As now can be understood, accurate preload measurements can be obtained using the fastener of the present invention since there will be no slippage between the transducer and the fastener during torquing and in addition, assurance will be had that optimum echo signals will be obtainable. Moreover, subsequent measurements can be readily made with the same transducer to recheck for preload and to measure and monitor for cracks and flaws and for acoustic emissions.

The embodiments of FIGS. 2–4 have advantages over that of FIG. 5 in that the noise signal 125 will be eliminated or minimized.

Although pulse-echo techniques were described in making measurements employing the fasteners of the embodiments of FIGS. 2–5, it is to be understood that the embodiments of FIGS. 2–5 may be used in obtaining preload measurements employing resonant frquency techniques.

I claim:

1. A fastener for fastening together structural members comprising:
   a shank having a head at one end and threads formed at the other end,
   a shallow opening formed in one end of said fastener and having a maximum depth from said one end of said fastener which is substantially less than the length of said fastener, and
   an acoustic transducer located in said opening and permanently secured therein with said transducer being acoustically coupled to said fastener,
   the entire portion of said fastener between said opening and the end of said fastener opposite said opening being formed of solid metal throughout.

2. The fastener of claim 1, wherein: said opening is formed in said head and has a depth less than the length of said head as measured along the longitudinal axis of said fastener.

3. The fastener of claim 1, wherein:
   said opening is formed in said other end of said shank.

4. The fastener of claim 1, wherein:
   said transducer comprises a disc shaped member secured in said opening such that its thin plane is substantially perpendicular to the axis of said shank.

5. The fastener of claims 1, 2, 3, or 4, wherein:
   said fastener is formed of metal,
   said transducer has electrodes formed at opposite ends thereof,
   one of said electrodes being in electrical contact with said fastener, 6. A method of attaching two members together with a threaded fastener comprising the steps of:
   attaching said two members together with a threaded fastener having an acoustic transducer permanently attached to one end thereof,
   while said fastener is being torqued in place, employing said transducer to obtain measurements indicative of stress on said fastener,
   continuing to torque said fastener in place until a desired preload stress value is obtained, and
   leaving said transducer permanently attached to said fastener after said two members are attached together with said fastener.

7. The method of claim 6 comprising the steps of:
   at a later date employing said transducer to make subsequent measurements.

8. The method of claim 7 wherein said subsequent measurements comprise:
   monitoring for flaws or cracks in said fastener.

9. The method of claim 8 wherein said subsequent measurements are obtained by:
   actuating said transducer to produce an acoustic pulse, and
   detecting for pulses reflected from the other end of said fastener.

10. The method of claim 8 wherein said subsequent measurements are obtained by:
    actuating said transducer to produce an acoustic pulse, and
    detecting for pulses reflected from surfaces other than from said other end of said fastener.

11. The method of claim 8 wherein said subsequent measurements are obtained by:
    detecting for acoustic pulses in said fastener.

12. The method of claim 7 wherein said subsequent measurements comprise:
    monitoring for acoustic emissions produced by said fastener or by surrounding structure.

13. The method of claim 6 wherein said measurements are obtained by:
    actuating said transducer to produce an acoustic pulse, and
    detecting for pulses reflected from the other end of said fastener.

14. A fastener for fastening together structural members, comprising:
    a shank having a head at one end and threads formed at the other end,
    an opening formed in one end only of said fastener,
    said opening being defined by side wall structure extending from said one end only of said fastener to a substantially flat surface substantially parallel to the end of said fastener opposite said opening,
    the maximum distance between said one end only of said fastener and said surface of said opening being substantially less than the length of said fastener, and
    an acoustic transducer located in said opening and permanently secured therein with said transducer being acoustically coupled to said fastener,
    the entire portion of said fastener between said opening and said end of said fastener opposite said opening being of solid metal throughout.

15. The fastener of claim 14 wherein:
    said substantially flat surface of said opening is substantially perpendicular to the longitudinal axis of said fastener,
    said transducer has substantially flat opposite ends which are substantially parallel to said substantially flat surface of said opening and to said end of said fastener opposite said opening.

16. A fastener for fastening together structural members, comprising:
    a shank having a head at one end and threads formed at the other end,
    an opening formed in one end only of said fastener,
    said opening being defined by side wall structure extending from said one end only of said fastener to a surface which forms the end of said opening in said fastener,
    the maximum distance between said one end only of said fastener and said surface of said opening being substantially less than the length of said fastener, and
    an acoustic transducer located in said opening and permanently secured therein with said transducer being acoustically coupled to said fastener,
    said transducer having substantially flat opposite ends which are substantially perpendicular to the longitudinal axis of said shank
    the entire portion of said fastener between said opening and the end of said fastener opposite said opening being of solid metal throughout.

17. The fastener of claim 16, wherein:
    said substantially flat opposite ends of said transducer are substantially parallel to said end of said fastener opposite said opening.

18. The fastener of claims 14, 16, 17, or 15, wherein:
    said acoustic transducer is formed of a piezoelectric material.

19. The fastener of claims 16 or 17 wherein:
    one of said ends of said acoustic transducer is acoustically coupled to said surface of said opening.

20. The fastener of claims 1, 14 or 16 wherein:

said fastener is intended for use on aircraft or on spacecraft.

21. The fastener of claims 14 or 16, wherein:
said fastener is intended for use on aircraft or on spacecraft,
said opening is formed in said head,
said one end only of said fastener being the end of said head,
said maximum distance between said end of said head and said surface of said opening being less than the length of said head as measured along the longitudinal axis of said fastener,
said shank being of solid metal throughout its length.

22. A fastener, comprising:
a shank having a head at one end and threads formed at the other end,
a shallow opening formed in one end only of said fastener,
an acoustic transducer located in said opening and permanently secured therein with said transducer being acoustically coupled to said fastener,
said fastener being formed of metal with the portion of said fastener between said opening and the end of said fastener opposite said opening being of solid metal throughout.

23. The fastener of claims 1, 14 or 16 wherein:
said transducer is located in said opening such that it may be used for pulse-echo measurements wherein when said transducer is pulsed, a transducer signal is generated which travels from said transducer through said fastener to said end of said fastener opposite said opening and back to said transducer at least once,
the distance between said transducer and said end of said fastener opposite said opening being equal to a major portion of the length of said fastener such that when said signal is generated, it will travel through the entire gripping length of said fastener, including the portion of said shank next to said head, when traveling between said transducer and said end of said fastener opposite said opening.

24. The fastener of claim 23, wherein:
said opening is formed in said head only.

25. A fastener, comprising:
a shank having a head at one end and threads formed at the other end,
an opening formed in said head from the end of said fastener coinciding with the end of said head,
said opening being defined by side wall structure extending from said end of said fastener coinciding with the end of said head to a surface which forms the end of said opening in said fastener,
the maximum distance between said end of said fastener coinciding with the end of said head and said surface of said opening being less than the length of said head as measured along the longitudinal axis of said fastener,
an acoustic transducer located entirely in said opening and permanently secured therein,
said fastener being formed of metal with the portion of said fastener between said opening and the end of said fastener opposite said opening being of solid metal throughout,
said acoustic transducer being acoustically coupled to said surface of said opening,
said acoustic transducer having two electrodes,
one of said electrodes being electrically coupled to said fastener,
the other of said electrodes being located to be electrically connectible to a utilization device.

26. A method of attaching two members together with a metal fastener of the type comprising a shank having a head at one end and threads formed at the other end with a shallow opening formed in one end of said fastener, and an acoustic transducer located in said opening and permanently secured therein, the portion of said fastener between said opening and the end of said fastener opposite said opening being of solid metal throughout, said method comprising the steps of:
attaching said two members together with said fastener,
while said fastener is being torqued in place, pulsing said transducer to generate transducer signals to obtain measurements indicative of stress on said fastener,
continuing to torque said fastener in place until a desired preload stress value is obtained, and
leaving said transducer permanently secured in said opening of said fastener after said two members are attached together with said fastener.

27. A fastener, comprising:
a shank having a head at one end and threads formed at the other end,
a shallow opening formed in one end only of said fastener,
an acoustic transducer located in said opening and permanently secured therein with said transducer being acoustically coupled to said fastener,
said transducer being located in said opening such that it may be used for pulse-echo measurements wherein said transducer is pulsed, a transducer signal is generated which travels from said transducer through said fastener to the end of said fastener opposite said opening and back to said transducer at least once,
the distance between said transducer and said end of said fastener opposite said opening being equal to a major portion of the length of said fastener such that when said signal is generated, it will travel through the entire gripping length of said fastener, including the portion of said shank next to said head, when traveling between said transducer and said end of said fastener opposite said opening,
said fastener being formed of metal with the portion of said fastener between said opening and said end of said fastener opposite said opening being of solid metal throughout.

28. A fastener, comprising:
a shank having a head at one end and threads formed at the other end,
a shallow opening formed in one end only of said fastener,
an acoustic transducer located in said opening and permanently secured therein with said transducer being acoustically coupled to said fastener,
said transducer being located in said opening such that it may be used for pulse-echo measurements wherein when said transducer is pulsed, a transducer signal is generated which travels from said transduer through said fastener to the end of said fastener opposite said opening and back to said transducer at least once,
said fastener being formed of metal with the portion of said fastener between said opening and said end of said fastener opposite said opening being of solid metal throughout.

29. The fastener of claim 27, wherein:
said opening is formed in said head only.

* * * * *